US010392802B2

(12) United States Patent
Kreizinger

(10) Patent No.: US 10,392,802 B2
(45) Date of Patent: Aug. 27, 2019

(54) POLYURETHANE FOAM BACKED PANEL

(71) Applicant: Kenneth R. Kreizinger, Fort Lauderdale, FL (US)

(72) Inventor: Kenneth R. Kreizinger, Fort Lauderdale, FL (US)

( * ) Notice: Subject to any disclaimer, the term of this patent is extended or adjusted under 35 U.S.C. 154(b) by 0 days.

(21) Appl. No.: 16/161,146

(22) Filed: Oct. 16, 2018

(65) Prior Publication Data

US 2019/0112810 A1 Apr. 18, 2019

Related U.S. Application Data

(60) Provisional application No. 62/573,746, filed on Oct. 18, 2017, provisional application No. 62/618,111, filed on Jan. 17, 2018.

(51) Int. Cl.
| | |
|---|---|
| *E04C 2/38* | (2006.01) |
| *E04B 1/92* | (2006.01) |
| *E04C 2/28* | (2006.01) |
| *G01N 3/32* | (2006.01) |
| *B32B 13/04* | (2006.01) |
| *B32B 5/18* | (2006.01) |
| *E04C 2/284* | (2006.01) |

(52) U.S. Cl.
CPC .................. *E04C 2/38* (2013.01); *B32B 5/18* (2013.01); *B32B 13/045* (2013.01); *E04B 1/92* (2013.01); *E04C 2/284* (2013.01); *G01N 3/32* (2013.01); *B32B 2266/0278* (2013.01); *B32B 2307/3065* (2013.01); *B32B 2307/558* (2013.01); *B32B 2607/00* (2013.01)

(58) Field of Classification Search
CPC ... E04C 2/38; E04C 2/284; B32B 5/18; B32B 13/045; B32B 2307/558; B32B 2307/3065; B32B 2266/0278; B32B 2607/00; G01N 3/32; E04B 1/92
USPC ........................................................ 52/309.7
See application file for complete search history.

(56) References Cited

U.S. PATENT DOCUMENTS

| | | | | |
|---|---|---|---|---|
| 3,248,758 | A | * | 5/1966 | Schmitz .............. B29C 33/0033 249/134 |
| 3,258,889 | A | | 7/1966 | Butcher |
| 3,641,724 | A | | 2/1972 | Palmer |
| 3,715,417 | A | | 2/1973 | Pope |
| 4,122,203 | A | | 10/1978 | Stahl |
| 4,748,781 | A | | 6/1988 | Wencley |

(Continued)

FOREIGN PATENT DOCUMENTS

| | | | | |
|---|---|---|---|---|
| FR | 2473679 A1 | * | 7/1981 | ............. B60R 19/22 |
| WO | WO-2013022069 A1 | * | 2/2013 | ......... B29C 44/0469 |

OTHER PUBLICATIONS

Impact Resistance of Advanced Framed Wall Systems with Insulating Sheathing as the Primary Sheathing Research Report—0603, 2006 by Joseph Lstiburek and Peter Baker Building Science Corporation 70 Main Street Westford, MA 01886 P: 978.589.5100 F: 978. 589.5103.

*Primary Examiner* — Jeanette E Chapman

(57) ABSTRACT

A foam backed composite panel having two or more layers of materials adhesively bonded to each other. The panel has a face layer and an optional core layer with both made of any material except polyurethane foam. The panel's backside consists of a layer of exposed polyurethane foam and is supported by a frame. The foam backed panel is comprised on one or more layers of cast materials and has increased impact and fire resistance.

15 Claims, 2 Drawing Sheets

(56) References Cited

U.S. PATENT DOCUMENTS

| | | | |
|---|---|---|---|
| 4,914,883 A | | 4/1990 | Wencley |
| 5,080,950 A | | 1/1992 | Burke |
| 5,089,328 A | * | 2/1992 | Doerer ................ B32B 5/18 428/308.4 |
| 5,102,710 A | * | 4/1992 | Kaufman ............. B32B 5/18 428/71 |
| 5,512,233 A | * | 4/1996 | Gallagher ......... B29C 37/0032 156/245 |
| 5,580,501 A | * | 12/1996 | Gallagher ............ B29C 41/18 264/126 |
| 5,614,305 A | * | 3/1997 | Paine ................... B32B 5/12 428/301.1 |
| 5,736,221 A | | 4/1998 | Hardigg et al. |
| 6,436,521 B1 | * | 8/2002 | Lee ..................... C08J 9/0061 428/131 |
| 8,555,584 B2 | | 10/2013 | Cieperca |
| 9,919,499 B2 | | 3/2018 | Kreizinger |
| 10,261,037 B2 | * | 4/2019 | Sidhu ................... G01N 27/20 |
| 2002/0121787 A1 | * | 9/2002 | Tarahomi ......... B29D 99/0089 293/120 |
| 2002/0171164 A1 | * | 11/2002 | Halterbaum .......... B29B 7/42 264/53 |
| 2006/0019579 A1 | * | 1/2006 | Braunschweig ...... B24B 55/102 451/28 |
| 2006/0057406 A1 | * | 3/2006 | Darolia ................ C23C 14/22 428/469 |
| 2010/0222522 A1 | * | 9/2010 | Steele .................. C08J 3/005 525/420 |
| 2012/0011792 A1 | | 1/2012 | DeWildt et al. |
| 2012/0186742 A1 | * | 7/2012 | Kang .................... B32B 5/26 156/324 |
| 2015/0191909 A1 | | 7/2015 | Linares, III |
| 2018/0202159 A1 | | 7/2018 | Kreizinger |

\* cited by examiner

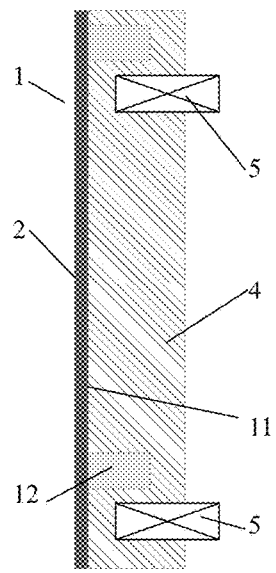
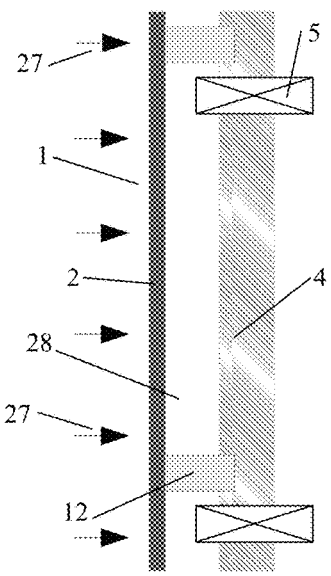
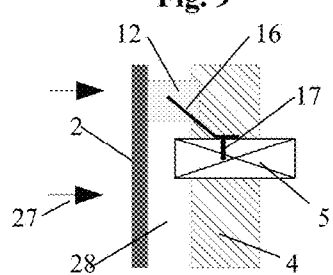
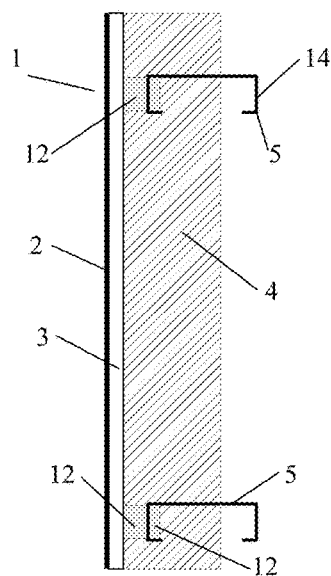
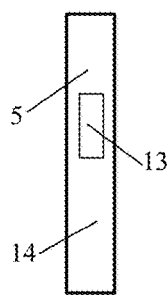
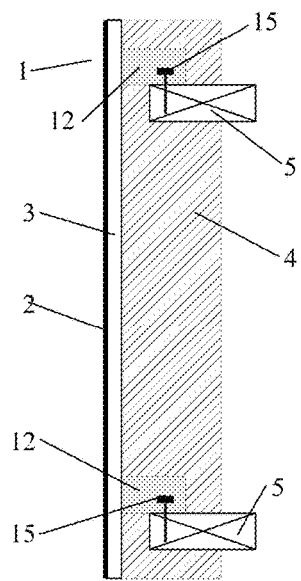

POLYURETHANE FOAM BACKED PANEL

CROSS REFERENCE TO RELATED APPLICATIONS

This application claims the benefit of the filing dates of U.S. Provisional Application Nos. 62/573,746, filed Oct. 18, 2017 and 62/618,111, filed Jan. 17, 2018, which are incorporated herein by reference.

INVENTION BACKGROUND

The inventive subject matter comprises the impact and fire resistance of polyurethane foam backed panels. Polyurethane foam backed panels are well known primarily for the thermal insulating properties foam brings to a wall or roof panel. Polyurethane foam has been sprayed into the cavities of framed walls and roofs and on top of roof substrates for decades to provide a high quality building insulation.

Polyurethane foam backed panels have also been known to provide some degree of flexural stiffness to a wall assembly. For example: U.S. Pat. No. 3,258,889 (Richard A. Butcher) discloses a structural wall comprised of polyurethane foam bonded to an interior wallboard and to the sides of studs and teaches added stiffness of the framed wall to enable thinner panels and lighter frame members. U.S. Pat. No. 3,641,724 (James Palmer) discloses a wall section comprised of an exterior cover bonded to the sides of stud members by a polyurethane foam that increases the strength of the entire structure. U.S. Pat. No. 4,748,781 & 4,914,883 (Stanley E. Wencley) discloses polyurethane fillets bonding a panel to frame members to provide an increased strength bonded structure. U.S. Pat. No. 5,736,221 (James S. Hardigg, et al) discloses two half panels with each having a face and a web molded to the face's backside and the webs bonded together to provide a panel having bending strength in all directions.

More recently polyurethane foam backed panels with unique frame supported configurations have been shown to produce significant structural qualities. For example US 20120011792 (Dean P. DeWildt et al) discloses a light-framed wall structure, comprised of sheathing attached to studs with a top and bottom plate and spray polyurethane foam in the cavity, has high axial point, lateral and transverse load bearing properties. In U.S. Pat. No. 9,919,499 I (Kenneth R. Kreizinger) disclosed a frame supported foam backed panel having substantial increased load capacity derived from increasing the bonding strength of the polyurethane foam bonded to both a cladding and supporting frame members. In pending US Application 20180202159 I disclosed that individual frame members of a supporting frame are greatly stiffened when polyurethane foam, of a foam backed panel, is bonded to both the top and the sides of frame members, i.e. is both continuous over a frame and in the frame's cavity.

However, no prior art teaches or even suggests that polyurethane foam can also greatly increase the impact resistance of a cladding or sheathing to which it is bonded to create a foam backed panel. In addition, no prior art teaches or even suggests fire resistant structural configurations for polyurethane foam backed panels. Finally, no prior art teaches a polyurethane foam backed sandwich panel with an insulating refractory core material and polyurethane foam as one of the panel's skin.

As such, one problem to be solved by this inventive matter is the use of polyurethane foam backing to increase a foam backed panel's impact resistance. A second problem to be solved is improving the fire resistance of polyurethane foam backed panels, since foam melts at a relatively low temperature, and thereby limits the foam's usefulness. A third problem to be solved is foam backed panel configurations that prevent polyurethane foam from melting when the face of the panels is subjected to fire.

SUMMARY OF INVENTION

The inventive subject matter comprises polyurethane foam backed panels which are defined as two or more layers of material(s) bonded together into a composite panel with the backside layer being polyurethane foam. These panels have a face material, i.e. cladding, on the front side, optional core material layer(s) and polyurethane foam bonded to backside of the face or to the backside of the last core material layer. In essence the panel has a face on the front side and exposed polyurethane foam on the backside. As such, the polyurethane foam backed panels may be a sandwich panel with a face material on the front side, polyurethane foam on the backside and a core comprised of any one or more material layers other than polyurethane foam.

Specifically excluded from this invention are precast panels consisting of a Portland cement concrete panel face or panel core layer to which a polyurethane foam layer is directly bonded, whether or not the precast panel has a supporting frame.

Several improvements to a polyurethane foam backed panel have been developed. First, when a sufficient thickness of polyurethane foam is bonded to the backside of certain claddings or sheathing, they have an increased impact resistance. Second, compact "fire spacers" have been developed to improve the fire resistance of foam backed panels and a third improvement is a panel configuration in which the core is comprised of an insulating refractory material having substantial thermal resistance. Such a relatively thin panel core material can prevent substantial heat generated from a fire on the panel face from reaching the polyurethane foam on the panel backside and thereby prevent the foam from melting.

Relative to greater impact resistance, it was found that despite polyurethane foam's low compressive strength and hardness, typical two pound density, closed cell polyurethane foam bonded to the backside of a cladding or sheathing greatly increases the impact resistance of the cladding or sheathing. The impact strength or toughness of a panel is determined by a falling, weighted object colliding into a stationary panel and the panel's impact resistance determined by a visual comparison of the impact damage done to a panel with polyurethane foam backing, to the impact damage to an identical panel without foam backing.

The significance of polyurethane foam providing impact resistance is that weaker, thinner and lighter claddings and sheathings can be substituted for more expensive stronger, thicker and heavier materials. This provides a significant cost savings since polyurethane foam can also provide insulation and an air, vapor and moisture barrier.

Relative to fire resistance, since polyurethane foam is known to melt at a relatively low temperature, improvements were sought to enable such a panel to resist fire. To this end, special fire spacers were developed for insertion into a foam backed panel to enable the panel to resist fire, especially in applications where polyurethane foam provides the sole bond of the panel to a supporting frame. In such cases a cladding or sheathing will fall away from a building when fire melts the polyurethane foam bonding them to the building's frame. To prevent this, refractory fire spacers were developed to provide a fire resistant bond between a refractory material panel core and a building frame. Specifically, a refractory material such as magnesium phosphate can withstand 2,000° F. heat and flames and when used as a panel core that is bonded to a building frame by fire spacers, the magnesium phosphate core remains intact and in place while withstanding a fire for more than an hour.

During development of the fire spacers, it was discovered that a magnesium phosphate binder can be combined with an insulating material filler to create an insulating refractory material capable of withstanding very high temperatures while also providing substantial thermal resistance. While such a material can be used as a foam backed panel core material to protect the foam from melting, the use of polyurethane foam bonded to the backside of such a core material causes heat buildup at the core/foam joint. This heat buildup results from polyurethane foam's much higher thermal resistance than that of the insulating refractory material. As the heat flows through the insulating refractory material having a R-value of about 1, it encounters the polyurethane foam having a R-value about six times greater, which causes the heat to build-up and temperature to rise when reaching the foam. Despite this obstacle, it was found that about a one inch thick insulating refractory core material provides sufficient thermal resistance, over a one hour test, to prevent polyurethane foam, on the core's backside, from melting when a fire is applied to the core's front side.

There were several unexpected results from the testing. First, it was unexpected that bonding a weak foam insulating material to the backside of a cladding or sheathing can substantially increase the cladding or sheathing's impact resistance. The advantage of such a finding is that thinner claddings or sheathings may be used without sacrificing impact resistance or panels are much more impact resistance with a polyurethane foam backing. This is especially advantageous since polyurethane foam performs other functions such as providing thermal insulation and is thereby results in a much more efficient utilization of materials and cost savings.

It was also unexpected that polyurethane foam bonded to the backside of an insulating refractory core material caused heat to buildup after it passed through the core. This resulted in requiring a slightly thicker core to further increase it's thermal resistance and prevent the foam from melting. Despite requiring a thicker core, it was unexpected to find that as little as one inch thick insulating refractory material could provide the thermal resistance to reduce a 1700° F. heat applied to a panel's face to only about 200° F. at the core's backside where a thermal barrier existed. The advantage of such a finding is that it enables a simple, inexpensive foam backed panel to attain a one hour fire rating. For example a panel, comprised of a thin claddings such as a coating applied to only a one inch thick refractory material core and backed by polyurethane foam bonding the core to a building frame, can attain a one hour fire rating.

It was also unexpected that fire spacers as small 2"×2" can sufficiently bond a refractory material panel to frame members. The advantage of this is that smaller fire spacers enable greater continuous foam for greater insulation. In addition fire spacers made of a refractory insulating material do not create an thermal bridge, although their thermal resistance is less than polyurethane foam.

It was also unexpected that refractory materials as thin as 0.25" thick can be used as a foam backed panel's core material to attain a one or more hour fire rating when bonded to a building frame with fire spacers also made of refractory materials. The advantage of this is that such refractory materials also provide a panel's cladding and/or sheathing and thereby result in a highly efficient utilization of materials and cost savings. Another advantage is light weight fire rated panels.

It was also unexpected that precast foam backed panels may be cast, removed from a form and handled in as little as one hour and that precast foam backed panels may use a single binder in two or more layers with each layer comprised of a different filler to product a different material properties.

Other objects, advantages and features of the inventive subject matter will be self evident to those skilled in the art as more thoroughly described below.

BRIEF DESCRIPTION OF THE DRAWINGS

FIG. 7 is a foam backed panel with fire spacers embedded in the polyurethane backing.

FIG. 8 is FIG. 7 showing the fire spacers supporting a panel face after a fire has melted the polyurethane foam that was also supporting the panel face.

FIG. 9 is a fire spacer strapped to a frame member after fire has melted some of the polyurethane foam of a foam backed panel.

FIG. 10 is a sandwich foam backed panel showing a fire spacer bonded to a panel core and attached to a steel stud.

FIG. 11 shows the front side of the steel stud of FIG. 10 with a hole through which the fire spacer material was cast to attach the stud to the fire spacer.

FIG. 12 is a sandwich foam backed panel with a fire spacer having an embedded bolt attached to a wood stud.

DETAILED DESCRIPTION ACCORDING TO THE PREFERRED EMBODIMENTS OF THE PRESENT INVENTION

The inventive subject matter comprises polyurethane foam backed panels which are defined as two or more layers of material(s) bonded together into a composite panel with the backside layer being polyurethane foam. These panels have a face on the front side, optional core material layer(s) and polyurethane foam bonded to backside of the face or to the backside of the last core material layer. In essence the panel has a face on the front side and exposed polyurethane foam on the backside. As such, the polyurethane foam backed panels may be a sandwich panel with a face material on the front side, polyurethane foam on the backside and a core comprised of any one or more material layer(s) other than polyurethane foam. As used herein, the term "foam backed panel" refers to the above described polyurethane foam backed panel.

Figure 1:
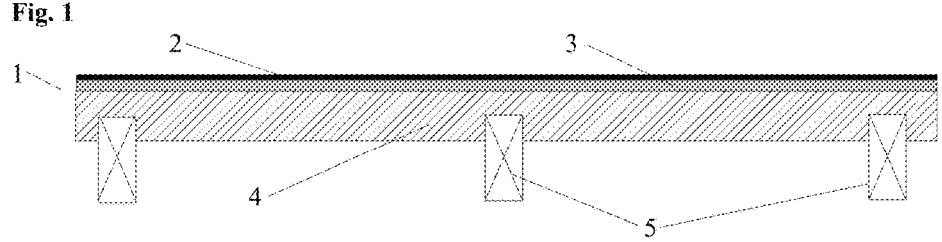
FIG. 1 is a sandwich, polyurethane foam backed panel having a panel face, a core bonded to the face and a polyurethane foam backside bonded to the core and to frame members.
Figure 2:
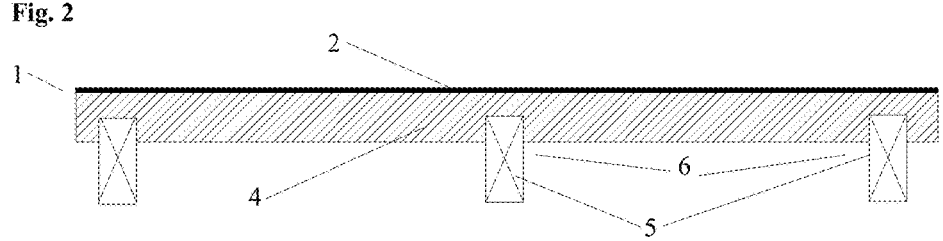
FIG. 2 is a two layer foam backed panel having a panel face backed by a layer of polyurethane foam that is also bonded to frame members.

FIG. 1 shows a sandwich foam backed panel 1 having a face 2, bonded to a core material 3 which is bonded to a polyurethane foam backside 4. The foam backed panel 1 is supported by frame members 5 that are embedded in and bonded to the polyurethane foam 4 and thereby bonded to the foam backed panel 1. FIG. 2 shows a two layer foam backed panel 1 comprised of a face 2 bonded to polyurethane foam backside 4 which also bonds the frame members 5 to the panel. A frame or frame members bonded to a foam backed panel are not considered to be "layers", even though they are part of the foam backed panel.

The layers of a foam backed panel are bonded together by adhesion or cohesion with a layer of polyurethane foam as the last or back layer, providing a backing to the prior layers. Adhesion is the action or process of adhering, i.e. sticking fast to a surface or substance and cohesion is like molecules sticking together, such as two layers having the same binder although different filler materials. Bonded or bonding as used herein shall only refer to an adhesive or cohesive bond.

A binder is any liquid or dough-like material or substance that holds or draws other materials together to form a cohesive whole by adhesion or cohesion and hardens into a solid. Binders are typically cast materials and include resins, Portland cement and phosphate cements for example. Unless otherwise noted, polyurethane foam referenced herein is a binder and is any self-bonding, liquid applied foam, made from polyurethane, polyisocyanurate or other chemicals in whole or in part, that is typically cast by spraying or pouring, expands and self-bonds to materials it comes in contact while it is expanding. While it is a self-bonding, adhesive foam, in some cases it may be desirable to use it in conjunction with a separate bonding material. The polyurethane foam is closed cell and has a density of less than four pounds per cubic foot and more preferably less than 3.2 pounds per cubic foot and even more preferably less than 2.5 pounds per cubic foot.

The panel face provides either an exposed finished texture or a base/backer board for an attached finished cladding. The polyurethane foam backside provides the panel with thermal insulation, an air, vapor and moisture barrier as well as increased load carrying capacity and impact resistance. The optional core may consist of one or more material layers to assist the panel in resisting loads, fire, insects, moisture and other items. The polyurethane foam on a panel's backside is considered to be "exposed" and comprises the panel's backside material. The exposed foam may be supported by a frame, although is not covered by another material such sheathing or a concrete wall. The polyurethane foam's exposed side may only be covered by a thin film or coating bonded to the foam. Any other foam cover bonded to the foam's backside becomes the panel's backside and renders the foam as being in the panel's core and thereby not a foam backed panel.

In one embodiment, a foam backed panel was found to have a dramatically higher impact resistance over an identical panel without polyurethane foam backing. Impact is herein defined as a high force applied over a short time period by a moving object, i.e. weighted object, colliding into a stationary panel. An impact test determines the impact strength or toughness of a material or panel and for purposes of this disclosure utilizes a falling or swinging object, i.e. weighted object, colliding into a stationary panel or an object launched from a cannon into a stationary panel. The term "applied impact" refers to an amount of force, as measured in in-lbs or ft-lbs, that is rendered on a panel during an impact test and results in impact damage, whether it be visible or not. The terms falling, swinging and launched describe different methods by which a weighted object is set in motion.

Impact resistance is determined by a visual comparison of the impact damage done to two identical panels with the exception that one panel is backed by polyurethane foam, at least in the area of the impact and the second panel has no polyurethane foam backing. The panel without foam backing is a control panel. A greater impact applied to the foam backed panel is compared to a lesser impact applied to the control panel, after which the impact damage to the two panels is visually compared. For example if an applied impact of 300 in-lbs rendered to a foam backed panel causes less visually ascertained damage than a 150 in-lbs applied impact to a control panel, then the foam backed panel has at least 100% more impact resistance than the control panel.

In impact testing a foam backed panel and a control panel it is important to be consistent in the testing procedure except for changing the applied impact rendered against the two panels. Both the control panel and the foam backed panel are to be tested over the same given span such that the applied impact is rendered on both panels in the same specific panel location, e.g. center of the panel width in the center of a 12 inch span. The only differences between the two panels and their testing is that the foam backed panel has polyurethane foam backing and is tested at a higher applied impact whereas the control panel does not have polyurethane backing and it tested at a lower applied impact. Panels may be impact tested with or without a supporting frame.

A polyurethane foam backed panel has increased impact resistance over an identical control panel, if the foam backed panel's impact damage is less than that of the control panel and the applied impact rendered on the foam backed panel is at least 25% greater and preferably at least 50% greater and more preferably at least 75% greater and even more preferably at least 100% greater and most preferably at least a 200% greater than the applied impact rendered on the control panel. Impact damage is defined as cracking, flaking, spalling, indentation, puncture and/or permanent deflection on the panel's front side and, after removing the foam from the foam backed panel's backside, the size and height of any cracks, protrusion or puncture on the backside of the panel's face or core, if present. Puncture is herein defined as the impacting object passing through one or more panel layers, although failing to penetrate all of the panel's layers. Impact testing may result in a control panel having visible impact damage while a foam backed panel to which it is compared has no visible impact damage.

A foam backed panel must have at least a one half inch thick layer of polyurethane foam and preferably at least one inch thick and more preferably at least two inches thick and even more preferably two and one half inches thick and most preferably at least a three inch thick layer of polyurethane foam on the panel's backside.

Penetration is herein defined as at least part of the impacting object fully penetrating all of the panels layers such that either the impacting object is implanted in the panel and visibly present on the backside of the panel or the impacting object fell away from or completely passed through the panel after impact and leaving a transparent hole through the panel. The degree of panel penetration by the impacting object is specifically excluded from the determination impact damages. Only the previously stated impact damages are to be considered whether or not the impacting object penetrated the panel. As such the impact resistance of a panel impacted by a 2×4 launched by a cannon, for example, can only be determined by a visual inspection of the previously stated impact damages caused to the panel and any distance to which the 2×4 penetrated the panel is irrelevant.

The impact testing herein is applicable to any foam backed panel that is or is to be supported by a frame. For testing comparison purposes any full sized foam backed panel or a foam backed panel installed in a building may have a foam backed section replicated and fabricated into a smaller sized panel of generally about one to four square feet in size. Such a smaller foam backed panel will be representative of the full sized or installed panel as long as the same materials, dimensions and general fabrication process are used. A control panel is then fabricated, identical to the foam backed panel, except without, i.e. less, the polyurethane foam backing. As such the only difference between the foam backed panel and the control panel to be tested is that the foam backed panel has a layer of polyurethane foam on it's backside whereas the control panel does not.

Only the composite panel section of a wall or roof assembly is subject to impact testing and therefore materials mechanically attached to the composite panel section are not to be included in the impact testing. For example brick mechanically attached to a foam backed panel are not to be included in an impact test, although brick bonded to a foam backed panel does comprise a layer of a composite panel and thereby are to be included in an impact test.

Testing has shown that the panel's length and width as well as the panel's impact location's proximity to a frame member can all affect the degree of impact damage. As such, it is important that a control panel be identical to a foam backed panel, except for the foam backing, to have a true resistance comparison.

Given the large variety of materials and material thicknesses that can comprise a layer in a foam backed panel, not every such panel will result in an increased impact resistance. It is highly doubtful that a three inch brick bonded to a backer board will have any greater impact resistance with an additional layer of polyurethane foam. The significance of this impact resistance embodiment is that weaker, thinner and lighter claddings and sheathings can be substituted for the more expensive stronger, thicker and heavier materials. Moreover, a layer of polyurethane foam has the added advantage of providing insulation and an air, vapor and moisture barrier.

The below testing has shown that two pound density, closed cell, spray (or poured) polyurethane foam of at least 0.5" thick, when bonded to a back of a cladding or sheathing enables the cladding or sheathing to resist substantially greater impacts. Moreover, the thicker the polyurethane foam backing, the greater the impact resistance to the point that the impact resistance can be several times that of the same sheathing without foam backing.

Figure 3:
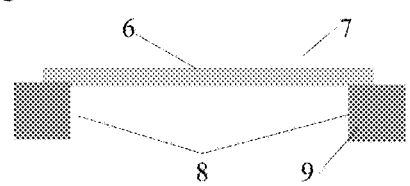
FIG. 3 is a supported control panel comprised of a oriented strand board (OSB) to be tested for impact resistance.
Figure 4:
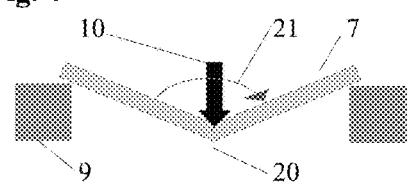
FIG. 4 is the control panel of FIG. 3 being tested for impact resistance.
Figure 5:
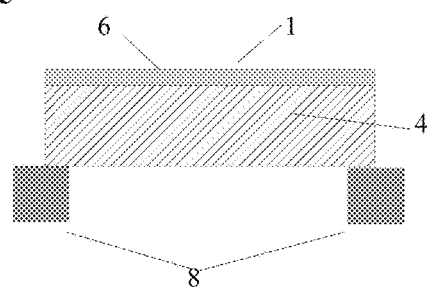
FIG. 5 is a supported foam backed panel identical to the control panel except also having a layer of polyurethane foam bonded to the OSB's backside.
Figure 6:
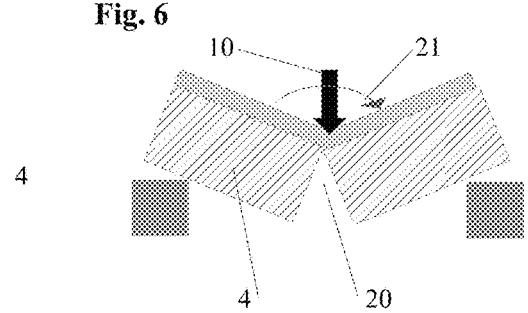
FIG. 6 is the foam backed panel of FIG. 5 being tested for impact resistance.

A first group of testing consisted of ½" OSB (oriented strand board) cut into six 6"×8" panels consisting of two control panels 7, as shown in FIGS. 3 and 4, comprised of only the OSB panel 6 and no polyurethane foam backing. Four other panels consisted of foam backed panels 1, as shown in FIGS. 5 and 6, and comprised of the same OSB panel 6 backed by of 2" thick, two pound density polyurethane foam 4 bonded to the OSB's backside. As shown in FIGS. 3 and 5 the panels were positioned face-up over a 6" clear span 8 with 1" of the 8" long panel supported by supports 9 each side of the span 8.

To test the panels for impact resistance, as shown in FIGS. 4 and 6, a 4 lb cylinder with a steel tip nose was used as a weighted object 10 dropped on each panel from various heights to produce an impact force, or an applied impact on the panels measured in in-lbs and that may result in impact damage 20. The impact force was applied to the center of the area of the panel that was over the span. In the first tests, the two control panels 7, were tested with applied impacts of 120 in-lbs (4 lb weight dropped from 30 inch height) and a 150 in-lbs impact respectively to determine the OSB's base impact resistance over the 6" span 8. The 120 in-lbs caused minor cracking on the first control panel's front side and no noticeable OSB bending. The 150 in-lbs force caused the second control panel 7 to sustain impact damage 20 of cracking on it's front side and split on it's backside to become permanently bent into about a 135° angular shape 21, as shown in FIG. 4.

In subsequent tests, three foam backed panels 1 were each positioned over the same 6" span 8 and an applied impact of 600 in-lbs, 480 in-lbs and 300 in-lbs was used for the respective tests. The 600 in-lbs test caused the polyurethane foam 4 backing to split into two sections and severely cracked and bent the OSB into about a 160° angular shape 21, as shown in FIG. 6. This foam backed panel clearly had more impact damage to the OSB than the control panel's 150 in-lb impact that resulted in a 135° bent shape. The 480 in-lbs test resulted in the foam backed panel's foam splitting and the OSB cracking, splitting and bending to somewhat less than the 135° bent shape caused to the control panel from a 150 in-lb impact.

The third foam backed panel was tested with 300 in-lbs applied impact over the same 6" span, neither the foam nor the OSB split, bent or even cracked and the only impact damage was a small 0.06" indentation into the OSB face. Clearly the impact damage resulting from 300 in-lbs applied impact to the foam backed panel was less than the impact damage caused by the 120 in-lbs impact to the control panel and substantially less than the 150 in-lbs applied impact to the second control panel.

A fourth foam backed panel test was a second test for the 480 in-lbs applied impact. This test result was similar to the first 480 in-lbs test, with the foam split the entire panel width perpendicular to the span and the OSB bent into about a 140° shape, which is slightly more than the control panel's 135° bent shape from the 150 in-lbs applied impact.

From these tests, it is apparent that 2" of polyurethane foam bonded to the backside of ½" OSB enabled the OSB to withstand a 300 in-lb impact better than the same OSB without foam backing could withstand a 120 in-lb impact. The testing also showed that it would take about 500 in-lb impact force on an OSB, with 2" foam backing, to withstand the same damage incurred by a 150 in-lb impact on the same OSB without foam backing. This represents a 233% increased impact resistance for OSB with the two inches of foam backing as opposed to the same OSB with no foam backing.

In another set of tests, a 0.25"×6.5"×27" panel comprised of a magnesium phosphate binder (MPB), a phosphate cement, was cast with 2 layers of fiberglass mesh reinforcement. The panel was cut into five sections 5.3" sections resulting in five 0.25"×5.3×6.5" panels. One MPB panel, selected at random, was left without a foam backing, i.e. the control panel, while the other four MPB panels were backed by 0.5", 1", 1.75" and 2.5" of polyurethane foam respectively. The five MPB panels were then impact tested over a 4.5" clear span with an applied impact made to the center of the area of the panel that was over the span.

When a 25 in-lb applied impact was dropped on both the MPB control panel and the 0.5" thick foam backed MPB panel, both panels split in half (except for the mesh). A 50 in-lbs applied force to the MPB panel with 1" of foam backing resulted in no panel damage although a 90 in-lbs applied impact to the same 1" foam backed MPB panel caused the panel to split in half. A 150 in-lbs applied impact to the MPB panel with 1.75" thick foam backing failed to cause the panel to crack or the foam split. Finally, a 300 inch-lb applied impact to the MPB panel with 2.5" thick foam backing resulted in only a smudged surface. From this series of tests, it is evident that a 0.5" thick MPB panel can have it's impact resistance increased by several times with polyurethane foam backing and the thicker the backing the greater the impact resistance.

In another impact test four 0.5" thick MBP panels were cut to a 6"×16" size with polyurethane foam bonded to the back of one panel to create a foam backed panel. The other three panels were left as is and served as control panels. The foam backed panel was placed on two supports 14" apart to create a 14" span and a 180 in-lbs impact was applied on the center of the panel over the span. The applied impact caused the foam to split and the panel to crack and bend to about a 160° angle. A first control panel was then positioned on the supports with the same 14" span and tested with a 50 in-lbs applied impact which resulted in a less severe crack and a panel bent to about 170°. Since the impact damage was not as severe as the foam backed panel, a second control panel was tested at 60 in-lbs and resulted in more impact damage than the first control panel, but still less damage than the foam backed panel. A third control panel was tested at 70 in-lbs and resulted in the same degree of cracking and bent angle as the foam backed panel. As such, the foam backed panel's impact resistance of 180 in-lbs was 257% of that of the control panel that had the 70 in-lbs applied impact.

In another series of impact resistance tests, three 7/16" thick OSB (oriented strand board) sheathing panels were attached to frames in three different configurations. The frames consisted of two 93" wood 2×4s studs, spaced 16" on center (14.5" clear span) and nailed to a top and bottom 2×4×17.5" plate. Two panels were configured with the 7/16"×16"×96" OSB sheathing nailed to frames with nail spacing at 8" around the entire OSB perimeter. One of these panels severed as a control panel while the cavity of the second panel was filled with 2" thick, two pound density spray polyurethane foam bonded to both the inside face, i.e. backside, of the OSB, and to the frame member's side. A third OSB panel and 2×4 frame were bonded together by the same polyurethane foam with the exception that 1" of foam was between the OSB panel and the top of the frame around the entire perimeter and the foam's thickness was 2" inside the frame's cavity, i.e. between the sides of the studs. In other words 1" of foam was continuous and 2" of foam was in the cavity formed by frames.

The framed OSB panels were all tested by dropping a 13.5 lb, 2" steel cylinder with a 1" steel ball tip welded to the cylinder's end. The cylinder, with ball tip down, was dropped from various heights onto the midpoint of the OSB panels between the 93" studs and at least 24" from the end plates. In the first OSB test, the cylinder was dropped from a 52 inch height to create a 702 in-lbs (13.5 lbs×52 inches) applied impact force on the non-foam backed OSB control panel. In this test only the cylinder's ball tip fully penetrated the OSB and the impact permanently deflected (i.e. bowed) the OSB 1/8" across the panel's 16" width. In a second test, on a different midpoint location on the same control panel, a 800 in-lb impact force was applied and both the ball tip and about 2 inches of the cylinder body fully penetrated the OSB.

The tests were continued on the second OSB panel that had 2" of polyurethane foam backing. In the first and second such tests a 1,400 in-lb and a 1,600 in-lb applied impact was made on the midpoint of the foam backed panel at separate locations. In both cases the impact damage comprised the full ball tip fully penetrating the OSB panel and into the foam, although the 2" cylinder body did not penetrate or even dent the OSB, nor did the OSB become bowed from either applied impact. As such the impact damage was less than that of the control panel and because the applied impacts were twice that on the control panel, the 2" foam backed OSB panel had more than twice the impact resistance as the OSB control panel. Moreover, after removing the foam from the backside of the OSB, it was visually apparent that the foam backed panel had less damage from the 1,600 in-lbs impact than the control panel had with the 800 in-lb impact.

Further testing showed that the cylinder dropped to create a 3,100 in-lb force fully penetrated the 2" foam backed panel but only penetrated 2" into the 3" foam backed panel. This again shows that the thicker the foam, the greater the impact resistance.

A panel is defined as a generally rigid structure, having some amount of flexural stiffness, such as sheathing or cladding that is supported by and covers a frame or frame members. Panels of this invention may be exterior panels, interior panels and of any size or shape. The panel's front side, i.e. its face or front skin, may be of any shape and the panel's backside, may have protrusions or indentations. A panel may be of any material or combination of materials not herein excluded and be of any size. Some examples of panels are: plywood, plastic or fiberglass sheets, sandwich panels, precast concrete, wood or foam boards, siding and roof panels, rib and similar protrusion backed panels, claddings, molded and corrugated or any combination hereof to name a few. A composite panel is defined as a panel comprised of two or more different materials bonded together in layers, such as a cladding or sheathing with a second material bonded to it's backside. While plywood, OSB, gypsum board and similar manufactured panels are composite panels in and of themselves, they may also provide a material layer in a foam backed panel.

Panels may be precast or prefabricated before being moved to their final installed position or they may be cast or fabricated in place, i.e. in their final installed position. Unless otherwise stated, cast shall mean both casting a liquid or semi-liquid such as wet concrete into a form or a previously cast, i.e. precast, panel. Panels may be attached to a previously installed frame or a frame may become part of a panel if the frame has one or more panels attached or bonded to it before being installed, i.e. becomes part of a building. For example a single precast panel may have a frame attached before the panel is installed and the frame becomes part of a the panel and called a framed panel. Or, several sheets of plywood may be attached to a frame before the frame is installed and the resulting structure is a framed panel.

Cladding is defined as any panel, material or combination of materials used to provide a front or outside cover for a panel or a framed structure. Cladding may be of any size and shape and of any material including panels, panel skins, siding, tiles, bricks, stones, shingles, aggregates, stucco, fiberglass, coatings, film, paint and other materials and even a foam's integral skin if the skin has a modulus of elasticity different than the foam's core. Coatings, film and paint are only considered a cladding if the total dried thickness is greater than 10 mils (0.01"). The cladding may be a panel itself, such as plywood or a foam board or may it be a part of a panel such as a coating applied to a foam board or a laminated panel. The cladding has a face, i.e. front side or exposed side, and a backside that is generally unexposed and is attached to a backing material and/or a frame.

Sheathing is herein defined as a separately installed panel or other covering over a frame that is covered by a separately installed cladding. Since a dried coating, film or paint of 10 mils (0.01″) or less are not claddings, sheathing covered by these materials is a cladding, unless the sheathing is covered by a separate cladding. Alternatively, if coating, film or paint of any thickness are applied to a separately installed panel which is not covered by a cladding, the resulting coated, film covered or painted panel is a cladding. When a framed structure has both a sheathing covered by a separately installed cladding, the combined sheathing and cladding are a cover.

A frame is any rigid structure formed of one or more relatively slender pieces, i.e. frame members, and used to support attached panels. Individual frame members have two ends, a front and back edge that is parallel to the cladding or sheathing and two or more sides that are generally perpendicular to the cladding or sheathing. Frame members may or may not be in direct contact with one another to form a frame. Cladding or sheathing may be in direct contact with a frame and bonded or fastened to a frame. A frame may also be embedded in polyurethane foam when at least some frame members have at least one edge and one side covered by and bonded to a polyurethane foam layer.

In another embodiment the foam backed panel is a refractory sandwich building panel comprised of a face, an insulating refractory core material and a polyurethane foam backing. One of polyurethane foam's weaknesses is that it has a low tolerance to heat and begins degradation at around 250° to 300° F., which is far below fire temperatures of 1000° to 2000° F. and higher. Therefore, especially in cases where a foam backed panel is attached to a building by the panel's polyurethane foam backing bonded to the building's frame, precautions must be taken to protect the foam and/or building from fire.

ASTM E119 is a wall assembly fire test requiring at least part of a wall structure to remain in place for one or more hours when subjected to a fire. Specifically, ASTM E119 is a pass-fail test based on a wall assembly's, including a wall panel's, ability to prevent a water stream from penetrating into the wall's interior side immediately after the wall's exterior side has been subjected to fire flames, high temperatures and gases for 60 minutes or longer. The test is for one, two, three and four hours and determines whether some portion of the assembly or panel remains standing as a barrier capable of preventing the water stream from passing through the wall. Under such a test it is not uncommon for much of the wall assembly to be destroyed or severely damaged from the fire.

Using ASTM E119 as a basis to determine fire protection, it has been found that an insulating refractory core material, when formed as a slab, may be of such a thickness that it's thermal resistance prevents a fire's temperature on it's front side from increasing on it's backside to a temperature that causes the foam bonded to the slab's backside from melting. Thermal resistance is the temperature difference between the slab face and backside that induces a unit heat flow rate through a unit area of the slab.

Although, simply because an insulating refractory material has the thermal resistance to substantially reduce the temperature on it's backside from the heat of a fire on it's face, i.e. front side, does not necessarily prevent foam bonded to the backside from melting. Testing has shown that when polyurethane foam is bonded to the backside of a slab having a lower thermal resistance than the foam, a temperature resistant barrier is created at the slab's backside. Basically the foam provides an increased thermal resistant which causes the heat to become trapped or "bottled up" at the slab's backside and the temperature begins to rise since the heat's flow is severely restricted by the foam. As shown in the below test results, any heat flowing from the slab's face to backside encounters substantial resistance when it reaches the polyurethane foam bonded to the backside and the resulting increased temperature at this core/foam joint must be accounted for in determining the insulating refractory core material's thickness.

For example, a one inch thick slab comprised of a magnesium phosphate binder with a 3:1 by weight binder to vermiculite filler was tested. In a first test, the one inch slab was subjected to a flame ranging from 1740° F. to 1810° F. applied the slab's face over 60 minutes, while the slab's backside temperature was recorded. Beginning at the ambient temperature of 82° F. the backside's temperature increased to about 117° F. over the first 20 minutes and then remained within two degrees of 117° F. for the next 40 minutes.

In a second test of the same one inch thick slab, a two inch thick two pound density polyurethane foam was bonded to the slab's backside. In this test a thermometer was inserted through the foam to the slab's backside to record the temperature at the slab/foam joint. As the temperature of the flame applied to the slab's face was raised from about 1200° F. to 1750° F. over a 60 minute period, the temperature on the slab's backside increased from an ambient 85° F. to 197° F. in 30 minutes and then leveled off at about 207° F. over the final 30 minutes. After 60 minutes the fire was extinguished although the slab's backside temperature continued to rise for about 6 minutes reaching a peak of 230° F. When the foam was cut away from the slab's backside it was revealed that the 230° F. was insufficient to melt any of the foam.

In comparing these two tests, the existence of the foam bonded to the slab's backside caused the temperature to buildup to about twice that of an open aired backside. As such, it is apparent that the temperature on the slab's backside can be considerably higher when foam is bonded to the slab's backside as opposed to an open aired backside. Moreover, the greater the difference between the thermal resistance of the slab and foam the greater the heat buildup on the slab's backside. As such, simply knowing a slab's thermal resistance will not necessarily determine whether or not foam bonded to the slab's backside will melt at any given temperature. Only after testing specific slab/foam combinations can it be known whether or not a fire applied to the face of a slab, of a certain material and thickness, is sufficient to prevent a certain foam, bonded to the slab's backside, from melting. No such testing or relationships have previously been established.

A similar test was conducted on a 1.1″ thick slab comprised of magnesium phosphate binder with an expanded clay filler and two inches of polyurethane foam bonded to the slab's backside. A 1,700° F. flame was applied to the slab's face for 60 minutes and the temperature on the slab's backside was recorded. The backside's temperature began at 80° F. ambient temperature and rose to 213° F. over the 60 minutes after which the flame was extinguished. While the backside's temperature continued to increase to 236° F. over the next 10 minutes, this temperature was insufficient to cause any of the foam from melting as determined when the foam was cut away from the slab.

In another test for a two hour fire rating pursuant to ASTM E119, a two inch thick slab comprised of magnesium phosphate binder with an expanded clay filler was mixed with water and cast into a form. After curing, two inches of polyurethane foam was bonded to the slab's backside and a thermometer placed through the foam to the slab's backside. A fire was positioned on the slab's face with temperatures beginning at 1100° F. and increasing to 1910° F. over 120 minutes, consistent with temperature increases prescribed by ASTM E119. The temperature on the slab's backside was recorded beginning at 82° F. ambient temperature and increased to 206° F. at 120 minutes, at which time the flame was extinguished and the temperature began to decrease. After the foam was cut away from the slab, it was revealed that none of the foam melted. As a result a two inch thick insulating refractory material slab prevented the melting of polyurethane foam bonded to the slab's backside.

Several similar tests were done using different face materials as well as different lightweight insulating fillers including vermiculite, perlite and expanded shale as well as different binders such as sodium silicate. In all cases the polyurethane foam bonded to the insulating refractory material core restricted the heat flow at the slab/foam joint which resulted in a much higher temperature than was recorded when the slab's backside was open aired.

In another test, a one inch thick mineral wool was tested with and without polyurethane foam bonded to it's backside. The Roxul #40320 mineral wool is rated with a 4.0 R-value and a thermal conductivity of about 0.04 W/(m K). In a first test, without polyurethane foam bonded to it's backside, a 1700° F. flame was applied to the mineral wool's face over 60 minutes and the temperature on the mineral wool's backside increased from 82° F. to 204° F. over the 60 minutes. In a second test, the same mineral wool had two inches of polyurethane foam bonded to it's backside. This mineral wool's face was then subjected to a flame starting at 1200° F. that was increased to 1600° F. over 45 minutes while the temperature on the mineral wool's backside was recorded. The backside's temperature rose from an ambient 92° F. to 400° F. over the 45 minutes at which time the fire test was stopped due to the foam's apparent melting. When the foam was cut away from the mineral wool, a 0.75" depth of melted foam was revealed.

This test revealed that the polyurethane bonded to the mineral wool's backside severely restricted the heat flow and thereby trapped the heat resulting in the polyurethane foam melting. Moreover, despite having a 4.0 R-value and a thermal conductivity of about 0.04 W/(m K), the mineral wool was insufficient to prevent the foam from melting on it's backside.

In another test a one inch thick panel of calcium silicate, manufactured by Johns Manville, having a thermal conductivity of about 0.10 W/(m K) was fire tested with 2" of foam bonded to it's backside. Temperature readings were taken every 10 minutes on the front face and the panels backside, inside the foam. In this test the face temperature reached 1720° F. at 50 minutes before ending at about 1690° F. at 60 minutes, at which time the backside temperature was 324° F. and continued to increased to 346° F. over 8 minutes after the fire was extinguished. In this case only about ⅛" of the foam melted.

FIG. 1 shows a sandwich foam backed panel 1 with a slab face 2, a core 3, which may be an insulating refractory material, and polyurethane foam 4 on the panel's backside that bonds the panel to frame members 5. While it is well known that the thicker the core 2, the greater it's thermal resistance, thicker cores cost more, are heavier and encroach on valuable interior floor area. As such, it is preferable to have as thin a panel core as possible to prevent the foam backing 4 from melting when the slab face 1 is subjected to certain degrees of fire.

While it is well known that material thickness is directly correlated to thermal resistance of a slab, the more important issue is the core material's fire resistance capacity. In other words, what is the minimum core thickness needed for a particular insulating refractory material to prevent the foam bonded to the slab's backside from melting when the face of the slab is subjected to one, two or three hour fire temperatures. Once an insulating refractory material's fire resistance capacity is known for a given fire rating, any additional material thickness serves no fire resistance purpose.

Insulating refractory materials are herein defined as a type of non-metallic material having an insulating R value of 0.5 or greater as well as those chemical and physical properties that make them applicable for structures, or as components of systems, that may be exposed to environments above 1,000° F. (811K; 538° C.).

There are a number of well known refractory binders that can be combined with various known high temperature resistant insulating materials, however there is no such known combination that meets the requirements of being relatively thin, impact resistant and sufficiently insulative to prevent foam from melting within a certain time duration. Examples of refractory binders are calcium aluminate cements, magnesium phosphate binders other phosphate based binders, sodium silicate (aka water glass) and more. When these and similar refractory binders are mixed with fillers such as lightweight aggregate materials including vermiculite, perlite, extend-o-spheres, bubble alumina and expanded clay, shale and slate they result in insulating refractory materials that provide thermal insulation. Such compositions typically have low density, low thermal conductivity and inferior mechanical strength to that of conventional castables. As used herein, the term "magnesium phosphate" is a binder mixed with one or more fillers and may include additives and be reinforced.

The fire resistance rating of some insulating refractory materials may be changed by altering the binder-to-insulating material composition or the density of the insulating refractory material. In addition, the building panel's face and core may consist of the same or a different insulating refractory material or part of a refractory material core may have a non-insulating filler, such as quartz, to increase the panel's impact resistance.

For purposes of this disclosure, an insulating refractory material's fire resistance capacity for a one hour fire ratings pursuant to ASTM E119 is limited to about 3" or less core thickness, and preferably about 2.5" or less core thickness and more preferably about 2" or less core thickness and even more preferably about 1.5" or less core thickness and most preferably about 1" or less core thickness. For a two hour fire ratings pursuant to ASTM E119 the core's thickness is preferably about 4" or less thickness, and more preferably about 3" or less thickness and even more preferably about 2.5" or less thickness and most preferably about 2" or less core thickness. For a three hour fire ratings pursuant to ASTM E119 the core's thickness is preferably about 5" or less thickness, and more preferably about 4" or less thickness and even more preferably about 3.5" or less thickness and most preferably about 3" or less core thickness. For purposes of the above thicknesses the term "about" shall be within an additional half inch of core thickness.

In another embodiment special fire spacers are embedded in the foam backed panels to enable the panel to resist fire, especially in applications where polyurethane foam bonds the panel to a supporting frame.

Testing has shown that a panel comprised of a magnesium phosphate binder (MPB) with fiberglass reinforcement, can withstand 2,000° F. heat and flames for more than one hour. In so doing the MPB panel remains intact and prevents flames from penetrating through it, although, in a foam backed panel, the high temperature can melt some or all of any polyurethane foam bonded to the MPB panel's backside. As would be expected, the depth of the foam melted varies with the panel's material composition and thickness. However, it was found that the increased temperature on the MPB's backside may limit the melting foam to that on or closest to the MPB and not affect the foam one, two or three inches away from the MPB. From this recognition a fire resistant spacer was developed to bridge this melting zone and thereby bond the MPB to the unaffected foam and to the building frame.

FIG. 7 shows a foam backed panel 1 having a cladding as a panel face 2 attached to a building's frame members 5, i.e. studs, by polyurethane foam 4 adhesively bonded to both the panel face's backside 11 and to the frame members 5. Also shown is a fire spacer 12 attached to the face's backside 11 and embedded in and adhesively bonded to the polyurethane foam 4. The frame members 5 are shown as partially embedded in and bonded to the polyurethane foam 4. In this configuration the fire spacer 12 is adhesively bonded to the frame members 5 by the polyurethane foam 4 which provides a thermal break between the panel face 2, fire spacer 12 and the frame members 5.

FIG. 8 shows the effect on the foam backed panel 1 of FIG. 7 after heat 27, generated by a fire, is placed against the panel's face 2 for an extended period of time. The heat moves through the panel face 2 and can melt the foam 4 on the panel face's backside 11 for a distance, which is referred to as a melting zone 28. This creates an open space between the panel's face 2 and the remaining polyurethane foam 4 beyond the melting zone 28, which was not affected, i.e. melted, by the heat 27. The width of the melting zone 28 is determined by the fire's temperature, the panel face's 2 thermal resistance, the foam's 4 melting point and whether or not the heat was fully contained.

FIG. 8 also shows the unaffected, remaining foam 4 bonded to the fire spacer 12 and to the frame members 5. Assuming the foam bond is sufficiently strong, this configuration will temporarily support the panel face 2 in place for at least one or more hours as required by ASTM E119.

If is important that the bond between the panel face 2 and the fire spacer 12 be able to withstand the fire temperature by either heat resistant adhesives or a fire spacer 12 with sufficient bonding strength cast directly onto the panel face's backside 11.

In another configuration, FIG. 9 shows a connecting object 16 embedded or otherwise attached to the fire spacer 12 and extending from fire spacer 12 to attach to the frame member 5 with a fastener 17. The connecting object 16 may be anything from a partially embedded strap to an embedded nut to which a bolt attaches the frame, to a cast binder material. Such a configuration is sufficient to temporarily hold the panel face 2 in place during a fire. In FIG. 9, it is not necessary that the fire spacer 12 extend to the foam 4, as long as the connecting object 16 is sufficiently stiff and can withstand whatever temperature exists between the fire spacer 12 and the foam 4.

In FIGS. 10 and 12, the fires spacers 12 are bonded directly to a panel core 3 and to frame members 5. In FIG. 10 the frame members 5 are steel studs having a flange 14 through which the fire spacer 12 is bonded by casting the fire spacer material through a hole 13 on the steel stud's flange 14 facing the panel core 3 or panel face as the case may be. A stay-in-place foam form (not shown) may be placed between the steel stud and panel core 3 to contain the fire spacer material as it is cast in place. FIG. 11 shows the steel stud frame member 5 of FIG. 10 having a hold 13 punched through the stud's flange 14 with the hold 13 smaller than the flange 14. Since the fire spacer 12 cast material inside the steel stud is wider than the hole 13, the fire spacer 12 becomes embedded in the steel stud for a solid and strong connection.

FIG. 12 shows a similar configuration to FIG. 10 except the frame member is wood in FIG. 12 and has a bolt 15 screwed into the side of the wood frame member 5 that is also embedded into a cast-in-place fire spacer 12. Again, a stay-in-place foam form (not shown) may be used for casting the fire spacer 12 onto the panel core 3 and of sufficient height to embedded the bolt 15.

Fire spacers may be any shape or material that can withstand a fire's temperature and have a thermal conductivity of less than 2 W/(m K) and preferably less than 1 W/(m K). Materials having a higher thermal coefficient are specifically excluded as fire spacers due to their ability to cause thermal bridges through the insulation. Although, as stated above, metal straps, bolts and fasteners may be used to attach a fire spacer to a frame member.

In another embodiment the foam backed panels are precast and comprised of two or more or three or more layers of cast binder materials. Magnesium phosphate and polyurethane foam are complimentary materials in that when combined the resulting composite panel overcomes each material's weaknesses while enhancing their strengths. For example, magnesium phosphate is harder, more durable, fire and insect resistant, and can be used as a panel face, none of which applies to polyurethane foam, whereas polyurethane foam has high thermal resistance and is an air, vapor and moisture barrier, none of which applies to magnesium phosphate. On the other hand, both materials are relatively light weight, have excellent bonding strengths, are water resistant and setup very quickly. The result is a comprehensive wall or roof building panel, comprised of only two materials, and can be manufactured very quickly.

From a manufacturing perspective is is now possible to precast and then handle a sandwich building panel in less than one hour. For example, either a prefabricated cladding laid face down or a magnesium phosphate cast on a form as panel faces, can have a panel core layer of magnesium phosphate binder with an insulating refractory material filler, for example, cast on the panel face's backside within a few minutes. The core layer is followed, within 20 minutes, by a panel backside layer of polyurethane foam applied over the panel core material. The foam expands and hardens in minutes to enable a finished sandwich panel to be removed from the form and handled in less than 60 minutes from placing the panel face. During expansion the foam may optionally self-bond to a frame suspended above the applied foam.

Various additives and reinforcements may be added to the magnesium phosphate and the polyurethane foam and additional material layers may also be added such as spraying a thin film on the backside of the panel face or panel core to further resist moisture. In all cases it is important to ensure the sprayed material adequately bonds to the layer on which it is sprayed and also allows the next layer to adequately bond to the film.

In another configuration a Portland cement binder with various fillers may be cast in a form as a panel face followed by a layer of magnesium phosphate binder as the panel core and finally a cast polyurethane foam panel backside. In this case both the magnesium phosphate and the polyurethane foam self bond to the prior materials within minutes of the prior material's casting. However, the Portland cement panel face will require a much longer setup time before the panel can be removed from the form.

Precasting the various materials may be done by pouring or spraying the material in a generally horizontal form or by spraying the material into a tilted or vertical form. The cast materials may be self-bonding to the materials on which they are cast or an adhesive material may be applied between cast layers.

Another example of a precast foam backed panel is a multi-layered core comprised of the same binder that has different fillers in the different layers. For example a magnesium phosphate binder may use a quartz or fly ash filler in a front panel layer to increase a panel's impact resistance, and then use an insulating filler in a second core layer for fire resistant purposes. The second core layer may be immediately cast on a still wet first core layer and the common binder will bond the two layers together despite different fillers. As such the different filler materials result in the layers having different properties.

From the description above, a number of advantages of various embodiments of the polyurethane foam backed panel become evident:

(a) The inventive subject matter enables thinner, weaker and lighter claddings or sheathings to have substantial impact resistance by bonding an insulating foam material to their backside.

(b) Despite causing heat to be restrained and buildup as it encounters a panel backside layer of polyurethane foam, a relatively thin one inch layer of insulating refractory material has sufficient thermal resistance to prevent the foam, bonded to it's backside, from melting.

(c) A refractory insulating material such as magnesium phosphate backed by polyurethane foam produces a simple fire resistant foam backed panel capable of withstanding the heat from a fire for more than one hour.

(d) Fire spacers as small as 2"×2" can sufficiently bond a refractory material panel core, in a foam backed panel, to frame members such that the panel core remains in place during a fire to attained a one or more hour fire rating pursuant to ASTM E119.

(e) Fire spacers can bond a panel to a building frame without causing a thermal bridge.

(f) Refractory materials as thin as 0.25" thick can be used as a foam backed panel's core material to attain a one or more hour fire rating when bonded to a building frame with fire spacers.

(g) Insulating refractory materials in a foam backed panel enables lighter fire rated panels.

(h) Precast foam backed panels may be manufactured, removed from a form and handled within as little as one hour.

(i) Precast foam backed panels may use a single binder in two or more layers with each layer comprised of a different filler to product a different material properties.

Although the description above contains many specifications, these should not be construed as limiting the scope of the embodiments but as merely providing illustrations of some of several embodiments. Thus the scope of the embodiments should be determined by the appended claims and their legal equivalents, rather than by the examples given.

I claim:

1. A polyurethane foam backed panel having increased impact resistance comprised of:
   a. a foam backed panel with two or more layers of material(s) bonded together in a composite panel with a backside layer consisting of at least one half inch thick polyurethane foam, and
   b. said foam backed panel having impact damage rendered by an impact test with a first applied impact made at a specific panel location over a given span, and
   c. a fabricated control panel consisting of an identical foam backed panel, less said backside layer of said polyurethane foam, and
   d. said control panel having said impact damage rendered by said impact test with a second applied impact made at said specific panel location over said given span, and
   e. said first applied impact is at least 25% greater than said second applied impact, and
   f. said impact damage of said foam backed panel is less than said impact damage of said control panel as determined by a visual comparison,
   g. whereby said polyurethane foam backed panel has increased impact resistance.

2. A foam backed panel of claim 1 wherein said first and second applied impacts are made by an identical weighted object set in motion the same way.

3. A foam backed panel of claim 1 comprised of a cladding backed by said foam.

4. A foam backed panel of claim 1 comprised of a sheathing backed by said foam.

5. A foam backed panel of claim 1 comprised of a panel having one or more layers of cast binder materials.

6. A foam backed panel of claim 1 having three or more layers with a core layer comprised of cast magnesium phosphate.

7. A foam backed panel of claim 1 comprised of a supporting frame embedded in said polyurethane foam backside layer.

8. A method of testing an increased impact resistance of a polyurethane foam backed panel comprising,
   a. rendering an impact test with a first applied impact, made at a specific panel location over a given span, on a foam backed panel having two or more layers of material(s) bonded together into a composite panel with a backside layer consisting of at least one half inch thick polyurethane foam and resulting in impact damage on said foam backed panel, and
   b. fabricating a control panel identical to said foam backed panel, less said backside layer of said polyurethane foam, and
   c. rendering an impact test with a second applied impact on said control panel made at said specific panel location, over said given span and resulting in said impact damage and said first applied impact is at least 25% greater than said second applied impact, and
   d. visually comparing said impact damage on said foam backed panel with said impact damage on said control panel, and
   e. finding said impact damage on said foam backed panel is less than said impact damage on said control panel,
   f. whereby said polyurethane foam backed panel has increased impact resistance.

9. A polyurethane foam backed panel having increased impact resistance comprised of:
   a. a foam backed panel, with at least a one half inch thick polyurethane foam backside layer, having impact damage resulting from an impact test with a first applied impact made at a specific panel location over a given span and
   b. an identical, fabricated control panel, less said polyurethane foam layer, having said impact damage resulting from said impact test with a second applied impact made at said specific panel location over said given span, and
   c. said first applied impact is at least 25% greater than said second applied impact and said impact damage on said foam backed panel is less than said impact damage on said control panel, as determined by a visual comparison of said impact damages,
   d. whereby said foam backed panel has increased impact resistance.

10. A foam backed panel of claim 9 wherein said first and second applied impacts are made by an identical weighted object set in motion the same way.

11. A foam backed panel of claim 9 comprised of a cladding backed by said foam.

12. A foam backed panel of claim 9 comprised of a sheathing backed by said foam.

13. A foam backed panel of claim 9 comprised of a panel having one or more layers of cast binder materials.

14. A foam backed panel of claim 9 having three or more layers with a core layer comprised of cast magnesium phosphate.

15. A foam backed panel of claim 9 comprised of a supporting frame embedded in said polyurethane foam backside layer.

* * * * *